United States Patent [19]

Korb et al.

[11] Patent Number: 4,493,553
[45] Date of Patent: Jan. 15, 1985

[54] METHOD OF AND APPARATUS FOR MEASURING TEMPERATURE AND PRESSURE

[75] Inventors: Charles L. Korb, Potomac; James E. Kalshoven, Jr., Laurel, both of Md.

[73] Assignee: The United States of America as represented by the Administrator of the National Aeronautics and Space Administration, Washington, D.C.

[21] Appl. No.: 383,086

[22] Filed: May 28, 1982

[51] Int. Cl.³ .................... G01J 5/58; G01L 11/00
[52] U.S. Cl. ................................. 356/43; 73/705; 356/45; 374/137
[58] Field of Search ............ 356/43, 45, 73; 73/705; 374/120, 137

[56] References Cited

U.S. PATENT DOCUMENTS

| | | | |
|---|---|---|---|
| 3,632,212 | 1/1972 | Bernal | 356/45 |
| 3,734,620 | 5/1973 | Cade | 356/73 |
| 3,817,622 | 5/1974 | Billman et al. | 356/73 |
| 4,123,160 | 10/1978 | Caputo et al. | 356/43 |

FOREIGN PATENT DOCUMENTS 241752  9/1969  U.S.S.R. .................. 257/356

OTHER PUBLICATIONS

Kalshoven, Jr. et al., "Laser Remote Sensing of Atomspheric Temperature by Observing Resonant Absorption of Oxygen," Applied Optics, vol. 20, No. 11, Jun. 1, 1981, 1967-1971.
Mason, "Lidar Measurement of Temperature: A New Approach" Applied Optics, vol. 14, #1, Jan. 1975, pp. 76-78.
EOS Transactions, American Geophysical Union, Korb et al., vol. 60, No. 18, May 1, 1979.
9th International Laser Radar Conference on Laser Atmospheric Studies—Conference Abstracts, Korb et al., Jul. 2-5, 1979.
Engineering a Laser Remote Sensor for Atmospheric Pressure and Temperature, NASA Technical Memorandum 79538, Kalshoven, Jr. et al., Apr. 1978.
A Laser Technique for the Remote Measurement of Pressure in the Troposphere, 8th International Laser Radar Conference, Conference Abstracts, Korb, Jun. 6-9, 1977.

Primary Examiner—Vincent P. McGraw
Attorney, Agent, or Firm—John R. Manning; John O. Tresansky; Ronald S. Sandler

[57] ABSTRACT

In a method of and apparatus for making remote measurements of temperature and pressure in a gas, laser beams are transmitted through the gas to a reflecting target, which may be either a solid surface or particulate matter in gas or the gas molecules and the return beams are measured to determine the amount of energy absorbed by the gas. For temperature measurements, the laser beam has a wavelength whereat the gas exhibits a relatively temperature sensitive and pressure insensitive absorption characteristic, whereas for pressure measurements, the laser beam has a wavelength whereat the gas has a relatively pressure sensitive and temperature insensitive absorption characteristic. To reduce the effects of scattering on the absorption measurements, a reference laser beam having a weak absorption characteristic is transmitted colinearly with the data beam having a strong absorption characteristic. The two signals are processed as a ratio to eliminate back scattering that is common to the two beams. Various embodiments of transmitters and receivers are described for practicing the invention, such as a sequential laser pulse transmitter (20, 51) and receiver (68), simultaneous laser pulse transmitter (100) and receiver (116) and c.w. laser transmitter (134) and receiver (154).

31 Claims, 11 Drawing Figures

FIG. 8 SIMULTANEOUS PULSE TRANSMITTER

FIG. 6 SEQUENTIAL PULSE TRANSMITTER

SIMULTANEOUS CW RECEIVER

METHOD OF AND APPARATUS FOR MEASURING TEMPERATURE AND PRESSURE

ORIGIN OF THE INVENTION

The invention described herein was made by employees of the U.S. Government and may be manufactured and used by or for the Government for governmental purposes without the payment of any royalties thereon or therefor.

TECHNICAL FIELD

The present invention relates generally to temperature and pressure measurement, and more particularly, to a method of and apparatus for making remote measurements of temperature and pressure in air by transmitting laser beams at frequencies at which a gas, such as air, exhibits known pressure and temperature sensitive absorption characteristics, measuring said absorption and relating the result through physical equations to obtain accurate pressure and temperature measurements.

BACKGROUND ART

Temperature and pressure are typcially measured using temperature or pressure responsive probes located at a region of interest, such as at ground based meteorological installations or on aircraft. Applications of such direct measurement techniques are limited to only accessible regions of the atmosphere, and further could tend to interfere with the accuracy of the reading due to proximity of the measurement probe. There accordingly exists a need to provide remote pressure and temperature measurements.

Radiometric techniques have been applied to remote temperature measurement. In accordance with one technique, a tunable radiometer is made responsive to signals received in a predetermined portion of the millimeter frequency band to determine the power level of received signals at selectable frequencies within the band. The signals emanate from atmospheric molecules at power levels proportional to temperature. Various approaches are taken to determine air temperature in a predetermined volume of the atmosphere using techniques such as correlating the frequency to which the radiometer is tuned with air volume length since the distance through the atmosphere that radiation from gas molecules can travel is a function of frequency due to the frequency dependent absorption characteristics of atmospheric gases. As a practical matter, passive remote sensing techniques of this type obtain temperature measurements with vertical resolutions on only the order of a scale height with temperature accuracy of only 2°–3° C.

Infrared and microwave radiometers are currently providing vertical temperature profile information from satellites. This information has sufficient accuracy to enable climate modeling and weather forecasting only in the midtroposphere while exhibiting accuracies to only about 3° C. at the surface and tropopause. Further, passive radiometric techniques of the type currently being used in satellite based metereological research provide temperature as a function of pressure and thus require a reference altitude pressure to obtain a height profile. Currently, this information is typically obtained from forecasts since it could not heretofore be obtained from a satellite. No techniques, active or passive, for remotely measuring atmospheric pressure are known.

It is accordingly an object of the present invention to provide a method of and apparatus for remotely measuring temperature and/or pressure of a gas.

A further object is to provide a method of and apparatus for making remote measurements of temperature and/or pressure of air.

STATEMENT OF INVENTION

Gas temperature and pressure are measured by transmitting a laser beam through the gas at a selective wavelength whereat the gas has a relatively high temperature or pressure sensitive absorption characteristic, receiving the laser beam following reflection by a target and measuring relative energies of the transmitted and received beams. The term target can apply to a solid surface such as the ground or apply to a distributed volume such as particulate matter in the atmosphere or the gas molecules themselves. More particularly, to measure atmospheric gas temperature, the laser beam is at a wavelength at the center of a resonant absorption line with a relatively high ground state energy, whereat the gas exhibits a relatively temperature sensitive and relatively pressure insensitive absorption characteristic. To measure atmospheric pressure, the laser beam is at a wavelength in the wing of a resonant absorption line having a relatively low ground state energy of the gas, whereat the gas exhibits a relatively pressure sensitive and temperature insensitive absorption characteristic. These laser beams are defined as probe beams.

DETAILED DESCRIPTION OF THE INVENTION

In accordance with the invention, atmospheric pressure and temperature are remotely measured by transmitting laser beams through the atmosphere at wavelengths selected for relativey high temperature or pressure sensitive absorption characteristics, reflecting the laser beams from a target and receiving and processing the reflected beams to determine atmospheric temperature and pressure. It should be understood that the term target refers to a solid object, particulate matter suspended in gas, or the gas molecules themselves. Before describing the present invention in more detail, however, a discussion of the absorption characteristics of atmospheric gas and, in particular, oxygen within the A band, is necessary to help understand the theory upon which the present invention is based.

The molecules of a gas are formed of atoms that tend to resonate at a number of different frequencies depending upon the physical characteristics of the atom and the molecule such as the period of the orbiting electrons and several different modes of vibration and rotation of the molecule. The spectra correspond to the energy levels associated with that molecule. The energy, or resonance, levels represent the amount of energy each molecule absorbs or emits as the molecule changes states. Thus, when light passes through a gas, the molecules absorb some of the light, causing the molecule to jump to higher or excited states. The particular wavelengths of light absorbed by each type of molecule, such as oxygen, are unique, and if one were to frequency scan light passing through oxygen, one would observe a series of dark lines, known as an absorption spectrum, corresponding to the wavelengths absorbed. A more detailed discussion of the absorption characteristics of the oxygen A band is given in Burch and Gryvnak, "Strengths, Widths and Shapes of the Oxygen Lines Near 13,100 cm$^{-1}$ (7,620 Angstroms)", *Applied Optics*, Vol. 8, No. 7, July, 1969, pages 1493–1499.

Figure 1:
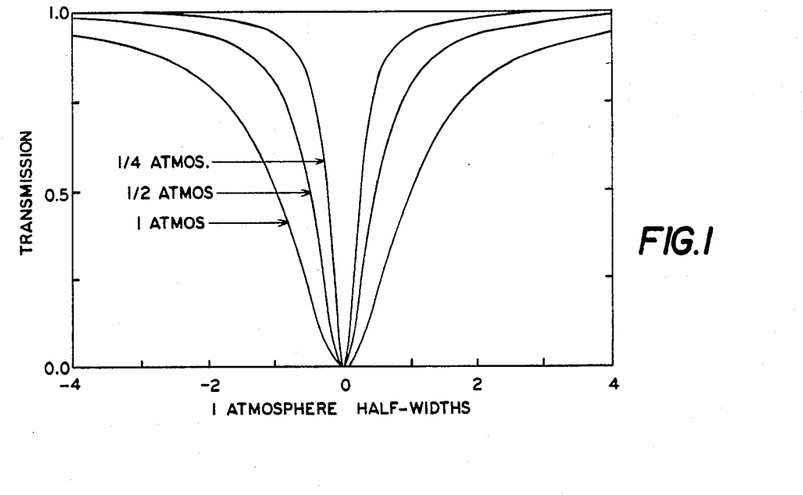
FIG. 1 is a graph illustrating light tranmission through a molecular resonant absorption line as a function of wavelength for different atmospheric pressures, showing that the absorption at line center changes little while it changes radically in the line wings.

The light transmission characteristics of the resonant lines of oxygen or other gases varies as a function of pressure and temperature. With reference to FIG. 1, showing the transmission characteristics of oxygen as a function of pressure, it is seen that the absorption at line center changes little while it changes radically in the line wings.

Figure 2:
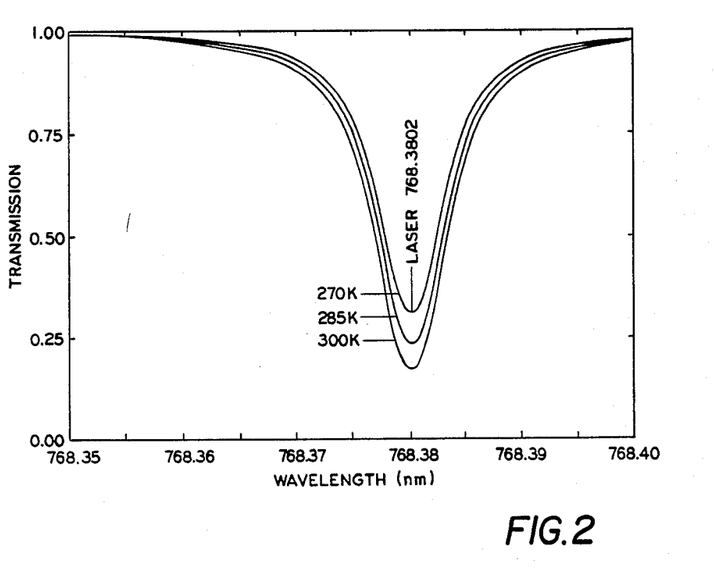
FIG. 2 is a graph showing light transmission through a molecular absorption line as a function of wavelength for different atmospheric temperatures, showing that this absorption at line center for the particular line changes radically.

With reference to FIG. 2, the transmission characteristic has a magnitude that varies primarily with temperature at line center while varying only minimally in the wings. In the oxygen A band, there are wavelengths that tend to be relatively temperature sensitive and pressure insensitive, and other wavelengths wherein absorption is relatively pressure sensitive and temperature insensitive.

Temperature or pressure data measurement can be implemented by either of two systems. In one, a pulsed laser system with a range-gated receiver (lidar) detects the backscatter returns from Mie and Ragleigh scattering off atmospheric gases and particulates along the laser path. This is analogous to a meterological radar system used for rain profiles but gives instead the temperature and pressure profiles along the laser beam path over increments limited only by the pulse duration and the sensitivity of the receiver system. In the second, a continuous wave laser system is aimed at a reflective target. In this case, an average pressure or temperature measurement along the path is obtained since incremental ranging information cannot be determined. A third, hybrid system is a continuous wave system with no solid target. Depending on atmospheric backscatter, an integrated path measurement is obtained. Although implementable, calibration is more difficult because of the variations in path length possible for a c.w. system with no fixed target.

For any of the above described laser systems, the energy received, I(R), after transmission of energy I(O) over a range R is given as:

$$I(R) = I(O)AB \exp\left[-2\int_0^R (S + K)dr\right] \quad (1)$$

where A is a constant which depends on the geometry of the system, B is the backscattered efficiency, the value of which depends on the reflecting medium, S is the attenuation coefficient of the atmosphere due to aerosol and continium absorption effects and scattering, and K is the absorption coefficient due to resonant absorption.

For a laser beam transmitted in a spectral region clear of resonant absorption lines:

$$I_R(R) = I_R(O)AB \exp\left[-2\int_0^R S\, dr\right] \quad (2)$$

where the subscript R refers to the reference beam. By taking the ratio of these two equations, common factors cancel out and dependence on only the resonant line absorption remains:

$$\frac{I(R)}{I_R(R)} = \frac{I(O)}{I_R(O)} \exp\left[-2\int_0^R K\, dr\right] \quad (3)$$

Any differences in the probe beam and reference beam characteristics (assumed identical in Eq. 3) would be accounted for by a calibration factor that is determined through an initial use of an independent temperature or pressure reference.

For a pulsed system where the signals are backscattered as a function of range, an analogous form of Eq. (3) results for measurements made at ranges $R_1$ and $R_2$ which allows the volume element from $R_1$ to $R_2$ to be isolated by taking the ratio of Eq. (3) at the range $R_2$ to Eq. (3) at the range $R_1$ which results in $$\frac{I(R_2)/I_R(R_2)}{I(R_1)/I_R(R_1)} = \exp\left[-2\int_{R_1}^{R_2} K\, dr\right] \quad (3a)$$

We note that the range $R_1$ can be at any distance from the transmitter, including the case of zero range, i.e., at the transmitter. The range $R_2$ must be larger than $R_1$.

The pressure and temperature dependence exist in K in Eq. 3. Therefore, taking the natural log of Eq. 3 and rearranging to obtain a form for K:

$$\int_o^R K\, dr = -\frac{1}{2} \ln\left[\frac{I(R)/I(O)}{I_R(R)/I_R(O)}\right] \quad (4)$$

Over a short distance, simplification is made by assuming that K is a constant and removing it from the integral:

$$K = -\frac{1}{2R} \ln\left[\frac{I(R)/I(O)}{I_R(R)/I_R(O)}\right] \quad (5)$$

It is noted that for the case of a stable transmitter with known output, the quantities I(O) and $I_R$(O) need to be measured only once and, henceforth, only I(R) and $I_R$(R) need to be measured thereafter.

For differential range measurements, an analogous form of Eq. (5) results which is $$K = \frac{-1}{2(R_2 - R_1)} \ln\left[\frac{I(R_2)/I_R(R_2)}{I(R_1)/I_R(R_1)}\right] \quad (5a)$$

It should be also noted that for differential range measurements which are found as shown in Eq. (5a), the laser transmitted signals, I(O) and $I_R$(O), as shown in Eq. (5), are not needed because they cancel in Eq. (5a).

The absorption coefficient is a function of the number density of the gas N(P,T) and the strength of the resonant line S(T):

$$K_\nu = N(P,T)S(T)F(\nu - \nu_0) \quad (6)$$

where $F(\nu - \nu_0)$ is the line shape function with line center frequency $\nu = \nu_0$. The density is given by:

$$N(P,T) = qWn_s\left(\frac{P}{P_s}\right)\left(\frac{T_s}{T}\right) \quad (7)$$

where q is the dry air mixing ratio of the gas being measured in the atmosphere (0.209 for $O_2$), n is the dry air number density at STP ($2.69 \times 10^{25}$ molec/m³), P is the pressure in millibars ($P_s = 1013.25$ mbar), and T is the absolute temperature ($T_s = 273.16$ K). An analytical expression for W, developed from water vapor tables found in handbooks, represents the effect of atmospheric water vapor:

$$W = 1 - 2.23 \times 10^9 \frac{H}{P} \exp\left(-\frac{5385}{T}\right) \quad (8)$$

where H is the relative humidity (H=1 for 100%). W is a small factor, contributing a 2% variation to Eq. (7) in the worst case of a hot humid day, decreasing rapidly to 0.5% in cooler conditions. Decreasing temperature as opposed to decreasing pressure being the dominant factor in Eq. (8) at high altitudes, the effect of W decreases even further. For oxygen, the line strength is:

$$S(T) = S(T_s)\frac{T_s}{T} \exp\left[1.439 E''\left(\frac{1}{T_s} - \frac{1}{T}\right)\right] \quad (9)$$

where $S(T_s)$ is the line strength at standard temperature, and E'' (in cm$^{-1}$) is the energy of the lower state of the transition.

The line shape function $F(\nu - \nu_0)$ is given by the Voigt integral which is a convolution of independent Lorentz and Doppler profiles arising from the effects of collision and velocity broadening, respectively:

$$F(\nu - \nu_0) = \frac{F'}{\sqrt{\pi}} \int_0^\infty \frac{\cos(xt)}{\exp(at + t^2/4)} dt \quad (10)$$

where $$F' = \frac{(\ln 2/\pi)^{\frac{1}{2}}}{\alpha_D} \quad (11)$$

$$a = \frac{\alpha_L}{\alpha_D} (\ln 2)^{\frac{1}{2}} \quad (12)$$

$$x = \left[\frac{\nu - \nu_0}{\alpha_D}\right] (\ln 2)^{\frac{1}{2}} \quad (13)$$

and $\alpha_D$ and $\alpha_L$ are the Doppler and Lorentz broadened half-widths, respectively. These are given as:

$$\alpha_D = \nu_0 \left(\frac{2kT\ln 2}{mc^2}\right)^{\frac{1}{2}} \quad (14)$$

$$\alpha_L = \alpha_L^s \left(\frac{P}{P_s}\right)\left(\frac{T_s}{T}\right)^n \quad (15)$$

where n is taken as 0.5 from kinetic collision theory, k is Boltzmann's constant ($1.38 \times 10^{-23}$ JK$^{-1}$), m is molecular mass ($5.31 \times 10^{-26}$ kg for $O_2$), and c is the speed of light ($3 \times 10^8$ m sec$^{-1}$). $\alpha_L^s$ is the collision halfwidth at standard temperature and pressure.

Placing Eq. 7 into tractable form has been treated extensively in the literature, especially in the *Journal of Quantitative Spectroscopy and Radiactive Transfer* published by Pegramon Press in Great Britain. For this invention, the form used is not critical since the effects measured are physical and the equations only serve to describe the temperature or pressure dependence. In accordance with one aspect of the invention, by having enough variation in conditions, for example, with a thermometer or barometer reference, the dependence of K could be found from Eq. 5 or 5a empirically without reference to theory.

One approach to reduce the theory to a form to allow analysis of the temperature effect is disclosed in Kalshoven et al, "Laser Remote Sensing of Atmospheric Temperature by Observing Resonant Absorption of Oxygen," *Applied Optics;* Vol. 20, No. 11, June 1981, pages 1967-1971 and makes use of the fact that measurements are made at line center, whereby it can be shown that Eq. 10 becomes:

$$F(0) = F'[\exp(a^2)] \left[ \frac{2}{\sqrt{\pi}} \int_a^\infty \exp(-z^2) dz \right] = \quad (16)$$

$$F' \exp(a^2)(1 - erf(a))$$

The value and range of "a" depends upon the molecular species being analyzed. For oxygen, $$a = 2.14 \times 10^5 \frac{\alpha_L^s}{\nu_o} \frac{P}{T} \quad (17)$$

Using values from Burch and Gryvnak, *Applied Optics*, Vol. 8, page 1493 (1969), for the temperature sensitive high J quantum number lines in the P branch of the oxygen A band, "a" is 3.0 at the earth's surface and decreases with altitude. The range of "a" allows an accurate analytical approximation to Eq. (16) to be developed using the tables for the error function:

$$F(0) = \frac{1}{3\alpha_L}\left[1 - \frac{\exp(1)}{10a}\right] \quad (18)$$

This expression for the line shape function at line center is accurate to better than 0.1% within a couple of kilometers of the earth's surface (a>1.7). Accuracy is better than 0.7% within the remainder of the troposphere (a>0.75). This expression was developed to show clearly the effects of pressure and temperature at line center.

Using the above relations, it can be shown that, at line center, the resonant absorption is $$K_0 = A_0 T^{-3/2} W \exp(-1.439 E''/T)\left[1 - \frac{(\exp(1))}{10a}\right] \quad (19)$$

where $$A_0 = \frac{qn_s}{3} T_s^{3/2} \frac{S(T_s)}{\alpha_L^s} \exp(1.439 E''/T_s) \quad (20)$$

The percent change of the absorption coefficient with percent change in temperature can be found by differentiating Eq. 19 and dropping the weak pressure dependent terms:

$$\frac{dK_0}{K_0} \approx \left(\frac{1.44E''}{T} - \frac{3}{2}\right) \frac{dT}{T} = g \frac{dT}{T} \quad (21)$$

Likewise, the sensitivity of the temperature determination to measurement errors in the constant term $A_0$ can be found:

$$\frac{dT}{T} \approx -\frac{1}{g} \frac{dA_o}{A_o} \quad (22)$$

Furthermore, variations in the other multiplicative factors in Eq. (19), i.e., W and the line shape factor $(1-e/10a)$, affect temperature through the same mathematical form as $A_0$ in Eq. (22).

As expected, Eqs. (21) and (22) show that the temperature sensitivity of a laser measurement will increase as higher energy lines are used, while there is a corresponding desensitization to both random and systematic errors. A tradeoff is made, however, since there is a loss in total absorption due to decreasing line strength at higher energy levels.

Given the absorption coefficient, the natural log of Eq. (19) can be rearranged to solve iteratively for temperature:

$$T_{n+1} = \frac{1.44E''}{\ln\left[A_0 W T_n^{-3/2}\left(1 - \frac{e}{10a}\right) K_0\right]} \quad (23)$$

This equation converges rapidly. The initial seed temperature is not critical. Thus, a value for $K=K_0$ can be determined using a dual laser system and Eq. 5 or 5a. This value is employed in Eq. 23 to find $T_n$.

Likewise, pressure can be found by finding a form for Eq. (10) for the line wings as opposed to line center. One representation is a power series expansion of the line width in terms of distance from the line center as $$F(\nu - \nu_o) = \frac{\alpha_L}{\pi(\nu - \nu_o)^2}\left[1 - \left(\frac{\alpha_L}{\nu - \nu_o}\right)^2 + \right. \quad (24)$$

$$\left. \frac{3}{2\ln 2}\left(\frac{\alpha_D}{(\nu - \nu_o)}\right)^2\right]$$

As may be seen from Eq. (24), at distances of greater than 5 line half-widths, the line profile is dominated by the first term of the series which is the form of the collision broadened line profile in the far wing of a line.

For horizontal path measurements of pressure using Eq. (5) or vertically orientated measurements of pressure at various heights using Eq. (5a), the absorption coefficient in the line wing can be found using Eqs. (6) through (9) and (24) as $$K = \left[\left(\frac{C}{(\nu - \nu_o)^2}\right)\left(\frac{P^2}{T^{2+n}}\right) e^{-E/kT}\right] * \quad (25)$$

$$\left[1 - \left(\frac{\alpha_L}{\nu - \nu_o}\right)^2 + \frac{3}{2\ln 2}\left(\frac{\alpha_D}{\nu - \nu_o}\right)^2\right]$$

where $$C = \frac{qT_s^{n+1} S(T_s)\exp(E/kT_s)\alpha_L^s}{\pi k P_o}$$

For the kinetic theory case of n=0.5, temperature desensitization of Eq. (25) is found at E=2.5 kT which gives an energy state of approximately 500 cm$^{-1}$ at 300 Kelvin. As given by Eq. (25), the pressure variation of the absorption coefficient is proportional to $P^2$ in the first term of the series with less significant higher order terms in $P^4$. Eq. (25) is in the form of a quadratic equation and can be solved for pressure using standard techniques.

Although the vertical pressure measurements could be made over individual atmospheric layers as described above, it is much more accurate and efficient to use an integrated path vertical measurement. In this case the measured absorption over the entire range from the laser to the atmospheric layer of interest is used. It is possible to use this approach since the pressure at various heights in the atmosphere is related by the hydrostatic equation.

The temperature dependence of the pressure measurement can be made small, in this case, by choosing absorption lines with energy levels near $E=(3/2)k\overline{T}$, where $\overline{T}$ is an appropriate average temperature for the path. For these lines, it can be shown that the integrated path absorption between the laser energy at altitude $Z_1$ and a second altitude $Z_2$ is given as $$\int_{Z_1}^{Z_2} K\, dz = \frac{b}{(\nu-\nu_o)^2}(P_2^2 - P_1^2)\left[1 - \frac{\alpha_L^2(\overline{T})}{2(\nu-\nu_o)^2}\frac{(P_2^2+P_1^2)}{P_o^2} + \frac{3}{2\ln 2}\frac{\alpha_D^2(\overline{T})}{(\nu-\nu_o)^2}\right] \quad (26)$$

where $P_2$ is the pressure at height $Z_2$, $P_1$ is the pressure at height $Z_1$, and the parameter b depends on the molecular parameters of the absorption line and has a weak residual dependence on temperature but can essentially be considered constant. Thus, the integrated path absorption coefficient is directly proportional to the square of the pressure to first order, with higher order correction terms which contribute only a few percent. Eq. (26) is a quadratic equation which may be solved for pressure at height $Z_2$ using standard techniques given the atmospheric pressure at the altitude of the laser.

The pressure determination using a wing measurement is not only extremely sensitive to pressure variations, but is also extremely sensitive to small laser frequency variations. The frequency stability required for an accurate determination of pressure can be reduced to only 0.01 cm$^{-1}$, an improvement of the order of a factor of 100, using a trough absorption region between two strong oxygen lines. The resulting absorption coefficient is flat over a significant frequency range, but still allows a measurement in the line wing to be made.

The integrated absorption coefficient of oxygen in the region near 13,153 cm$^{-1}$ has been calculated for a two-way atmospheric path from space to ground level, and also to various altitudes. Trough positions with significant absorption characteristics have been found at a number of frequencies, including the regions near 13,153.8 cm$^{-1}$, and 13,152.5 cm$^{-1}$. For these frequencies, analysis shows that the absorption is nearly independent of the atmospheric temperature structure.

The above equations assume the use of a narrow bandwidth laser system. The principles illustrated are the same regardless of the laser system bandwidth. However, above about 0.01 cm$^{-1}$ bandwidth, reduction of the basic line profile equation (Eq. 10) would be more difficult. Thus, the use of a narrow bandwidth system is preferred. To insure laser transmission at a known, desired frequency with known laser spectral line shape, the frequency and line shape of the transmitted, on-line laser signal may be monitored using etalons with the resulting signal being used to control the laser frequency.

Examination of the spectral region selected must be made carefully to avoid other unwanted resonant lines, such as isotopic lines. If present, they must be considered in the calculations. These can be analyzed employing Eq. 6 with the appropriate isotopic line parameters of strength, width and energy at the probe frequency. For the oxygen A band, these do not present any particular problem for the accuracy generally required.

Figure 3:
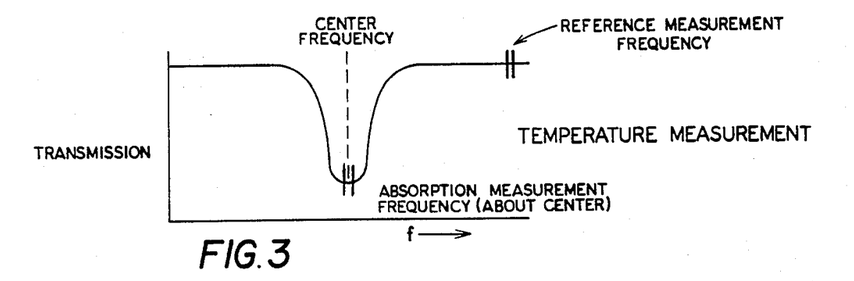
FIG. 3 is a graph illustrating the relative wavelength locations of the probe and reference beams for measuring atmospheric temperature in accordance with the invention.

Referring now to FIG. 3, to remotely sense temperature, in accordance with the invention, laser beams must be generated at two closely spaced frequencies to arrive at a value for K for use in Eqs. 4 and 5. One frequency is selected for its strong absorption characteristic using oxygen or other gas uniformly mixed in the atmosphere such that the absorption is highly temperature sensitive and relatively pressure insensitive, i.e., the "probe". As explained above, this corresponds to the region about the center of a gas absorption line with a high ground energy state. Lines in the oxygen (A) band with rotational quantum numbers J between 21 and 31 satisfy these conditions. Once the absorption line frequency is selected, i.e., a given choice of rotational quantum number, then a second or reference frequency, at which light is only weakly absorbed in the gas, is selected in the vicinity of the first absorption frequency. Generally, those weakly absorbed frequencies which are suitable as a reference frequency can be found between 0.3 and 1.0 Angstrom away from the absorption frequency.

A typical absorption line employed is the line at 12,999.95 wavenumbers (cm$^{-1}$) or the line at approximately 13,010.81 cm$^{-1}$. A typical reference frequency range for the 12,999.95 line is in the interval form 13,000.50–13,001.50. The typical reference frequency for the 13,010.81 line would be in the interval from 13,011.80–13,012.80 cm$^{-1}$. The system parameters are dependent on the accuracy required.

Figure 4:
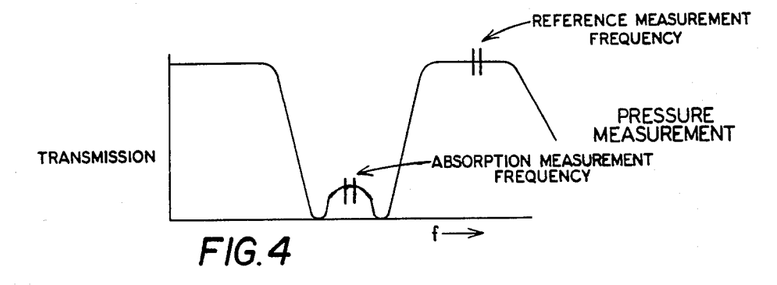
FIG. 4 is a graph showing wavelengths of probe and reference beams for measuring atmospheric pressure in accordance with the invention.

With reference to FIG. 4, to remotely sense pressure in accordance with the invention, laser beams composed of two closely spaced frequencies are transmitted into the atmosphere to a reflective target, either solid, aerosol or molecular. One frequency is selected for its strong absorption characteristic in oxygen or other gas such that the absorption is highly pressure sensitive and relatively temperature insensitive. As explained above, and as shown in FIG. 4, a measurement in a wing of a gas absorption line is pressure sensitive and further, if the gas absorption line has a relatively low ground state energy, a measurement at the wing position will also be temperature insensitive. A wing may be considered to be that region which is on the order of or greater than 1.5 line half-widths from the center frequency of a dominant absorption line, where the half-width is one half the width of the line as measured at half height on a plot of absorption coefficient versus frequency. Measurements in the wings of lines in the oxygen (oxygen "A") band with frequencies between 13,150 and 13,060 cm$^{-1}$, and between 13,050 cm$^{-1}$ and 13,080 cm$^{-1}$ generally satisfy these conditions. Additionally, with an upward or downward looking system, it is preferred to use lines with ground state energies in the range of from 250–300 cm$^{-1}$, and for horizontal systems, for the use of lines with ground state energies near 500 cm$^{-1}$ to achieve relatively optimum temperature insensitivity, the degree of which can be found through differentiation of Eq. 6 with respect to temperature.

The trough region is the region between strong absorption lines which generally falls in the wing of both absorption lines and which corresponds to the position of minimum absorption between these two lines. Thus, measurement in a trough region allows a measurement in the wing of an absorption line which is pressure sensitive and temperature insensitive if the frequency is one chosen for proper ground state energy, but which is additionally relatively insensitive to laser frequency instability (jitter) because the absorption in the trough is relatively flat with frequency. Three trough regions suitable for the measurement of pressure in a vertical looking system are near 13,152.2 cm$^{-1}$, 13,152.5 cm$^{-1}$ and 13,153.8 cm$^{-1}$. Thus, the measurement of absorption at, for example, 13,153.8 cm$^{-1}$, which has a relatively low average ground state energy of approximately 300 cm$^{-1}$, would be pressure sensitive, temperature insensitive and would be relatively unaffected by laser jitter of 0.01 cm$^{-1}$. Once the absorption line frequency is selected, a second frequency, serving as a reference frequency and which is only weakly absorbed, is selected in the vicinity of the first absorption frequency. Generally, these weakly absorbed frequencies can be found between 1.0 and 10.0 Angstroms away from the primary absorption frequency. The reference frequency need not be weakly absorbed in an absolute sense but only relative to absorption at the primary frequency in the frequencies noted above used for the pressure sensitive measurement.

For example, the primary frequency at 13,153.8 cm$^{-1}$ could use reference frequencies at either 13,152.2 or 13,152.5 or, alternatively, could use frequencies in the region outside the oxygen absorption band. As a second example, if either of the frequencies 13,152.2 cm$^{-1}$ or 13,152.5 cm$^{-1}$ is used as the primary frequency, then a reference frequency outside the oxygen band is preferred as the reference frequency to obtain sufficiently weak absorption compared to pressure sensitive primary frequency.

Figure 5:
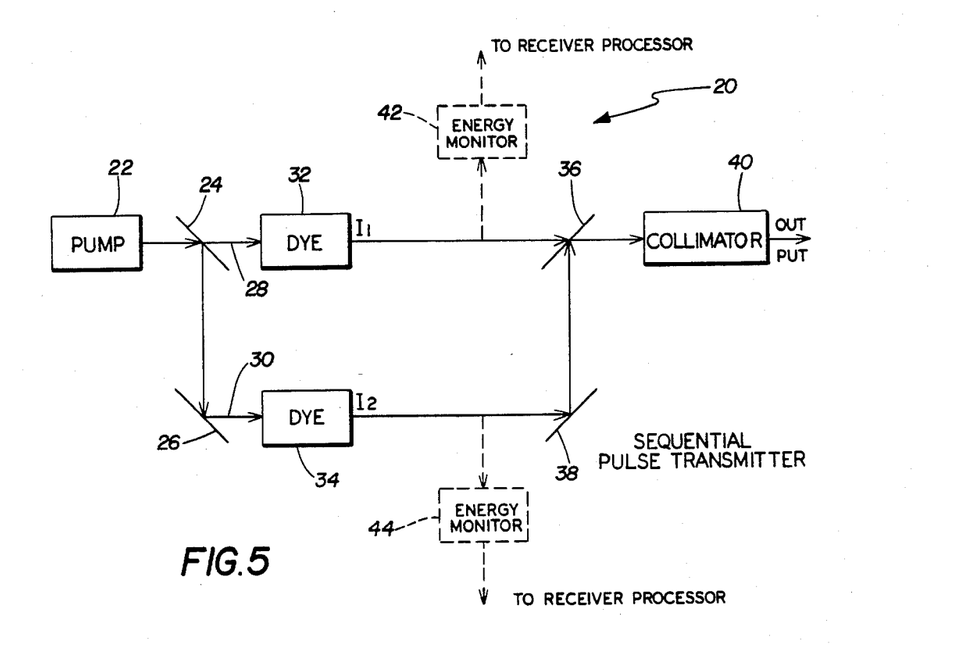
FIG. 5 is a simplified block diagram of a sequential pulse transmitter for making remote temperature and pressure measurements in accordance with the invention.

Referring now to FIGS. 5–11, various apparatus for implementing the remote atmospheric temperature and pressure measuring methodology discussed above shall now be described. Referring first to FIG. 5, a transmitter 20, in accordance with the invention sequentially transmits laser beams at strongly absorbed and weakly absorbed frequencies. It is understood that the transmitter 20 is operable in both remote temperature and pressure measuring modes, depending upon the frequency of the strongly absorbed output beam, i.e., whether it is at a frequency that is relatively temperature sensitive and pressure insensitive on the one hand or relatively pressure sensitive and temperature insensitive on the other. The transmitter 20 comprises a pulse laser pump 22 which may be a frequency doubled Nd:YAG or ruby laser, for example. The laser pump type employed depends on the organic dye used to provide desired laser wavelength with reasonable efficiency. The energy from pump 22 is split by mirror chopper 24 and mirror 26 into two paths 28, 30 respectively. The mirror chopper, mirror combination 24, 26 alternately energizes two different dye lasers 32, 34, one of which generates the strongly absorbed and the other of which generates the weakly absorbed frequency. The laser outputs are recombined into a single path with a second mirror chopper 36 and mirror 38 combination. The output of the mirror chopper, mirror combination 36, 38 is applied to a collimator 40 prior to transmission. Energy monitors 42, 44 measure the energy output of dye lasers 32, 34, respectively, to provide reference signal levels for normalizing received signals. Thus, the energy monitors 42, 44 account for the specific amount of energy generated by each dye laser 32, 34 to compensate for power output variations.

The dye laser 32, generating the strongly absorbed frequency, must be very narrow band and stable to avoid error. The reference beam laser 34, on the other hand, may be relatively broad band and less stable since the reference frequency is only weakly absorbed. If preferred, a single dye laser may be switched between alternate frequencies. The mirror choppers 24, 36 can be replaced by a beam splitter.

Figures 6, 7, 8:
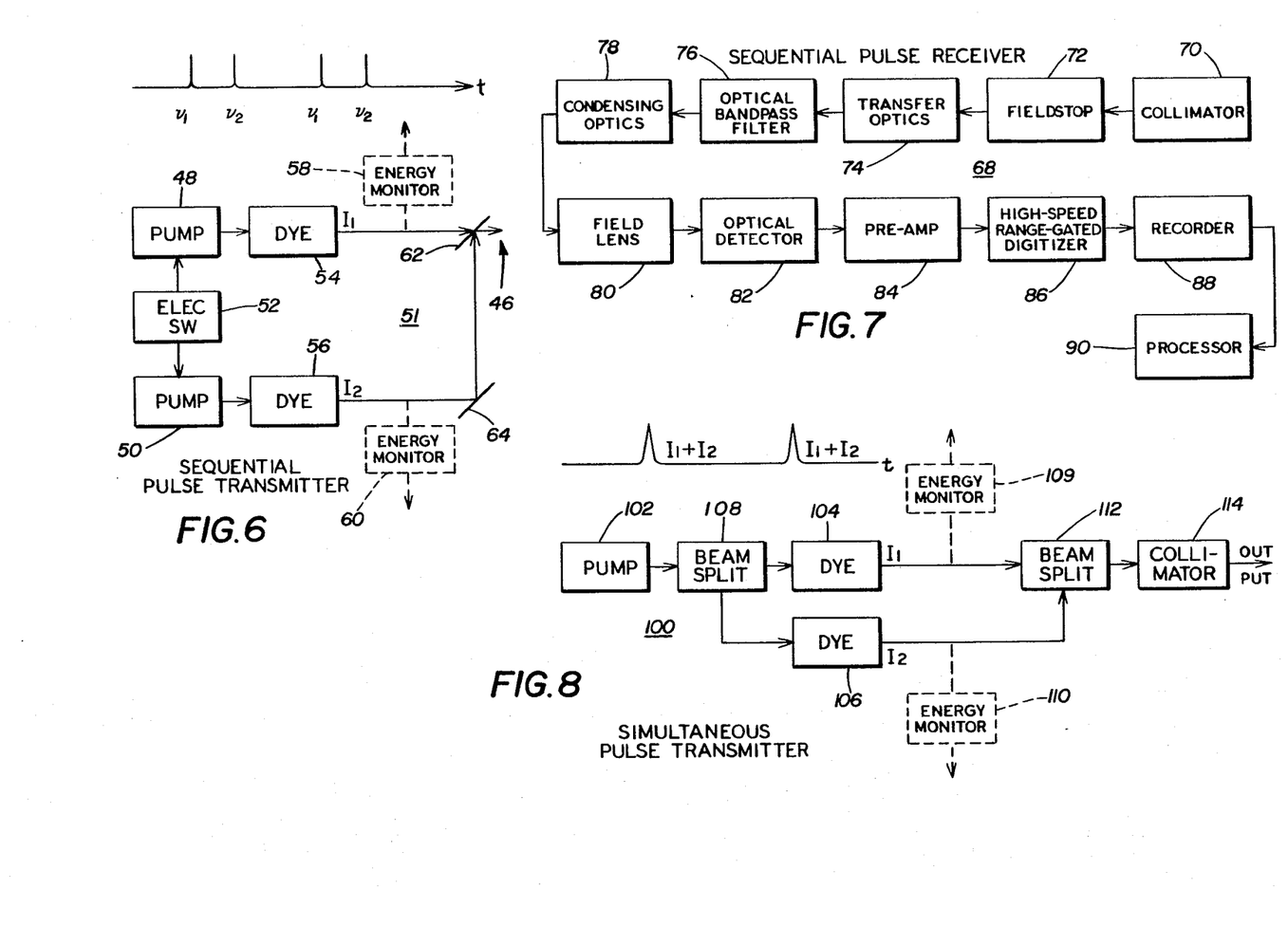
FIG. 6 is a simplified block diagram illustrating a second embodiment of a sequential pulse transmitter in accordance with the invention, together with a waveform showing exemplary output pulses.
FIG. 7 is a block diagram of a sequential pulse system receiver.
FIG. 8 is a block diagram, together with exemplary output pulses, of a simultaneous pulse transmitter for practicing the present invention.

An alternative transmitter system for generating sequential pulses, identified as 46 in FIG. 6, comprises a pair of pumps 48, 50 alternately switched on by an electronic switching circuit 52. The output of pump 48 is applied to dye laser 54 and the output of pump 50 is applied to dye laser 56. The outputs of dye lasers 54 and 56, measured by energy monitors 58, 60, respectively, are combined by mirror chopper 62 and mirror 64. One advantage of the transmitter shown in FIG. 6 over the one shown in FIG. 5 is that the FIG. 6 transmitter enables variable delays to be introduced between the successive laser pulses because switching is controlled electronically.

Referring now to FIG. 7, a sequential pulse receiver receives pulses generated by the transmitters of FIGS. 5 or 6 to enable processing using standard software to obtain temperature and pressure measurements as described above. Receiver 68 receives the incoming pulses by a collimator 70 which is essentially a telescope. The output of collimator 70 is supplied to a field stop 72 which is set at a size that will correspond to a field of view that is no less than the field of view of the transmitting collimator 40 for maximum efficiency. Transfer optics 74 follow the field stop 72 for collimating the beam to achieve a relatively planar wavefront required for input to an optical bandpass (spectral) filter 76 having a bandpass that will allow transmission of both of the two transmitted frequencies. Condensing optics 78, responsive to the output of filter 76, bring the received beam to a focal point. Field lens 80, located at the focal point of the condensing optics, eliminates the effect of spatial considerations in the field of view and focuses the beam on optical detector 82 which may be a photomultiplier tube or other light-to-electronic signal converter. The output of detector 82 is applied to a preamplifier 84 and thereafter to a high speed range gated digitizer 86 that converts the analog output signal from detector 82 into a number of selected adjacent narrow bin range gates and thereafter to a digital signal which indicates both the amplitude of the analog signal and the range gate in which the signal falls. Digitizer 86 may have as many as 2,000 range bins with the width of the range bins selectible from less than 6 nanoseconds to greater than 13 microseconds with typical values employed being 50-nanoseconds. In any event, the resulting digital signal is representative of the amplitude of the signal returned from the given range. Determination of which of the given transmitted frequencies is measured is accomplished by separating the pulses by a sufficient time such that the signal returned from the first pulse has dropped to a negligibly low value before energizing the second dye laser. The output of digitizer 86 is applied to an optional recorder 88 and processed in processor 90 to determine the I1/I2 signal ratios and calculate the atmospheric pressure and/or temperature at a given range in accordance with the algorithms (equations 23, 25 and 26) discussed above.

The system parameters are dependent on the accuracy required. Pulse widths from available pump lasers are generally 10 nanoseconds to 200 nanoseconds. Repetition rates vary typically from 1 hertz to 300 hertz. Typical pulse energies are about 0.1 joule/pulse for operation with narrow bandwidth (0.01 cm$^{-1}$).

Referring to FIG. 8, a transmitter 100 for transmitting simultaneous data (strongly absorbed) and reference (weakly absorbed) frequencies comprises a laser pump 102 having an output applied to dye lasers 104, 106 through a beam splitter 108. The dye lasers 104, 106 correspond to dye lasers 54, 56, respectively, in FIG. 6. The outputs of dye lasers 104 (I1) and 106 (I2) are combined, following monitoring by energy monitors 109, 110, in beam splitter 112. The colinear beams at the output of beam splitter 112 are applied to an output collimator 114. The simultaneous pulses $\nu_1$ and $\nu_2$ are shown in the waveform of FIG. 8. Thus, the simultaneous pulse system of FIG. 8 is different from the sequential pulse systems described above to the extent that the two beams $\nu_1$ and $\nu_2$ are generated simultaneously and that the corresponding dye lasers 104, 106 are energized simultaneously by a common laser pump 102.

Figure 9:
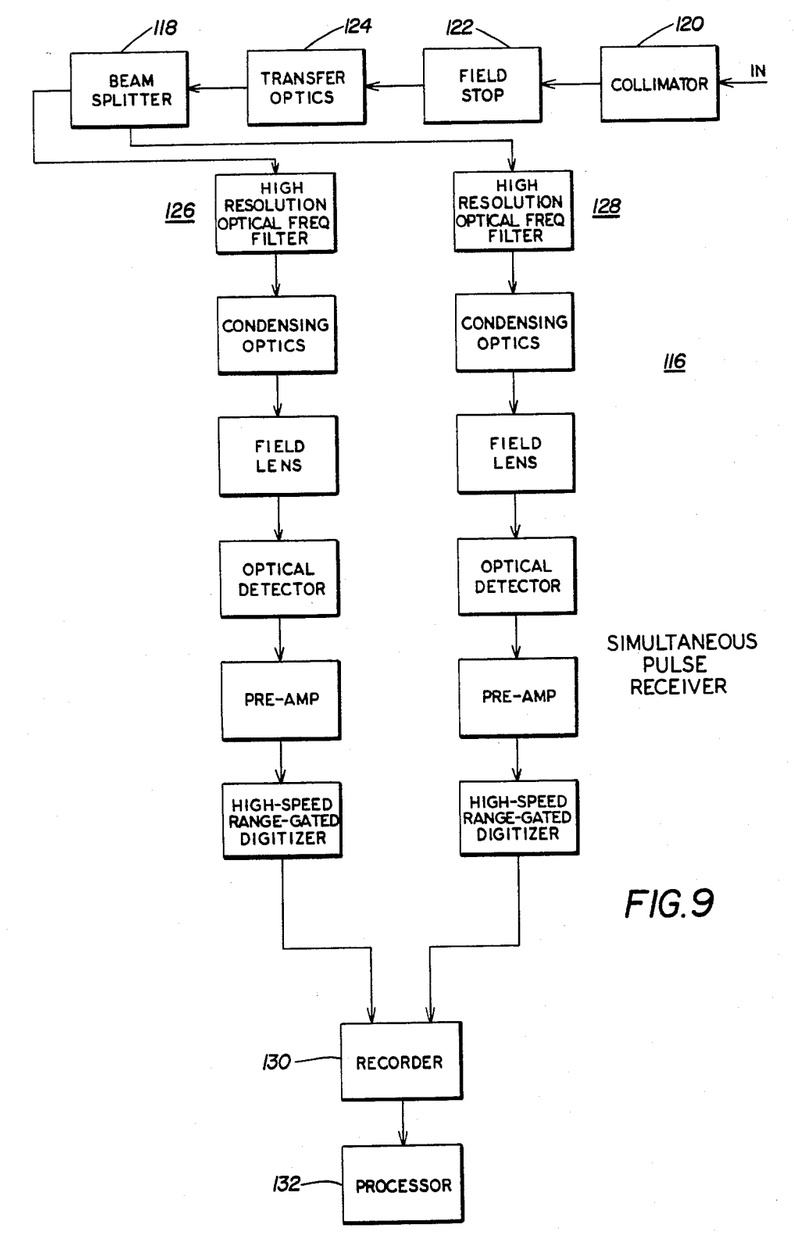
FIG. 9 is a block diagram of a receiver for receiving simultaneous pulses transmitted by the transmitter of FIG. 8.

A receiver for receiving the simultaneous laser beam pulses, illustrated in FIG. 9, is similar to receiver 68 shown in FIG. 7 except that similar signal processing elements must be provided in separate paths for the two beams following splitting of the data and reference beams by beam splitter 118. Thus, receiver 116 comprises an input collimator 120, a field stop 122 and transfer optics 124 similar to the corresponding elements in FIG. 7. Following beam splitter 118, the data and reference signals are individually processed along signal paths 126 and 128, respectively, before being combined in optional recorder 130 for processing in 132.

Figure 10:
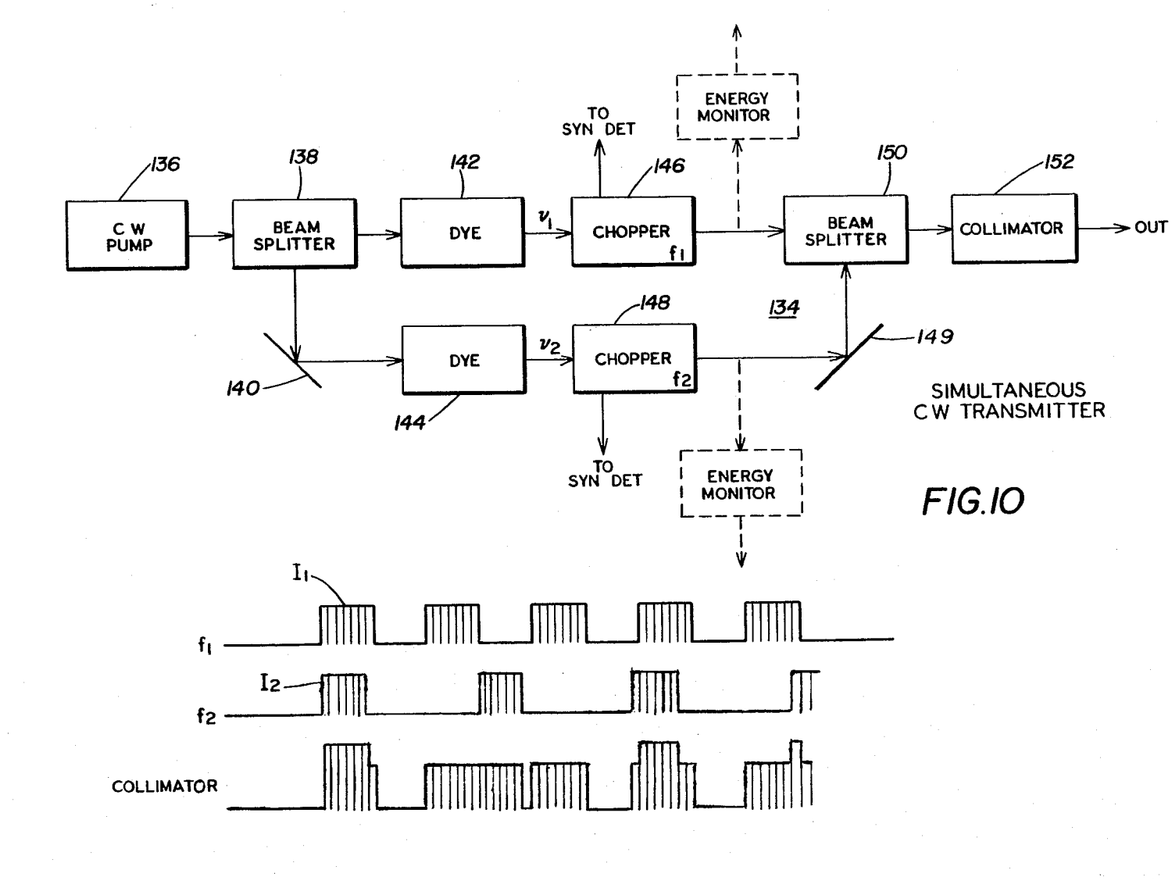
FIG. 10 is a block diagram, together with exemplary waveforms, of a simultaneous c.w. transmitter in accordance with the invention.

FIG. 10 discloses a transmitter for transmitting simultaneous c.w. laser beams to be reflected and received for processing to determine atmospheric temperature and pressure measurements. The transmitter 134 of FIG. 10 is similar to the simultaneous pulse transmitter 100 of FIG. 8. Differences relate to the use of c.w. efficient components for the pumps, dye lasers and choppers. Thus, the transmitter 134 comprises a c.w. pump 136 such as a krypton ion laser selected to induce lasing in dyes such as oxazine. The output of transmitter 134 is aligned with beam splitter 138. Following beam splitter 138, mirror 140 and dye lasers 142, 144, a pair of choppers 146, 148 develop a chopped signal to facilitate separation for processing the return signal. The chopping rate between the two choppers 146, 148 must be substantially different from each other and non-harmonic. Dye lasers 142, 144 are selected for efficient c.w. generation of the desired frequencies. The beam from laser 144, after chopper 148, is then reflected off of mirror 149. Following combination of the two laser beams in beam splitter 150, the colinear beams are collimated in output collimator 152 prior to transmission to a reflective target.

The choppers and collimator waveforms are also shown in FIG. 10. While the chopper and collimator signals are illustrated as being 100% modulated signals, modulation may be less than 100%.

Figure 11:
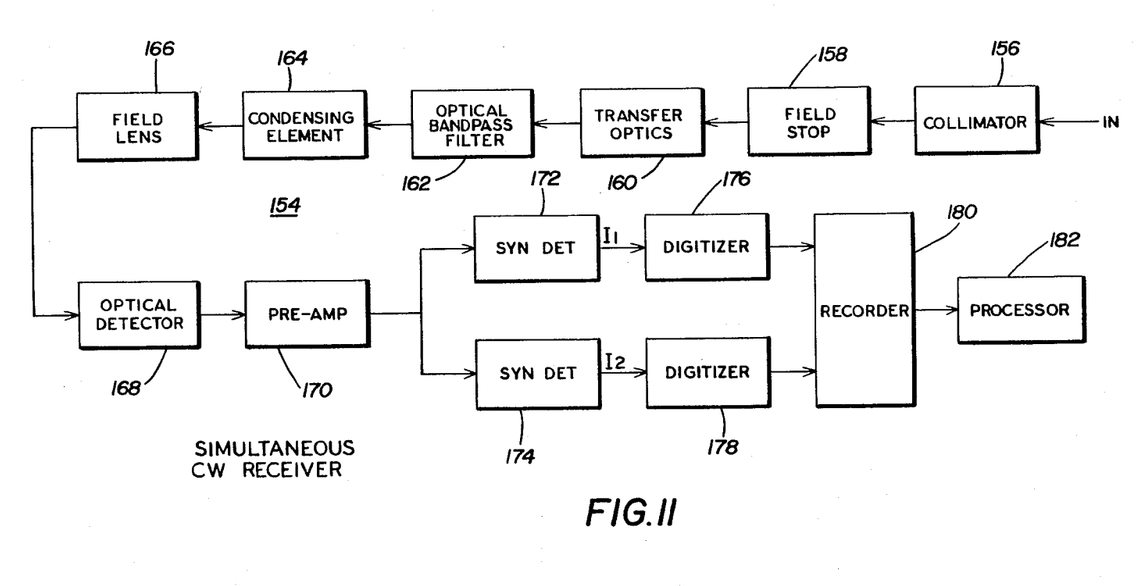
FIG. 11 is a block diagram of a receiver for receiving the c.w. signal developed in FIG. 10.

Simultaneous c.w. receiver 154, as shown in FIG. 11, includes input collimator 156, field stop 158, transfer optics 160 and other elements such as optical filter 162, condensing element 164, field lens 166, optical detector 168 and preamp 170 which are similar to corresponding elements discussed supra in connection with FIG. 7. The receiver 154 includes, however, a pair of synchronous detectors 172, 174 responsive to the output of preamplifier 170 and synchronized to choppers 146, 148 in transmitter 134 (FIG. 10). The signals from each transmitter chopper 146, 148 are used as sychronization signals for reference inputs to a corresponding phase-locked receiver (e.g., lock-in amplifier) for synchronous demodulation and detection. This allows for unambiguous electronic separation of the two laser frequencies. The outputs of synchronous detectors 172, 174 representing, respectively, data and reference signals, are applied to digitizers 176, 178 prior to optical recorder 180 and final signal processing in processor 182 to obtain temperature and pressure information.

Alternatively, a c.w. system could be implemented, although not shown, wherein two transmitted frequencies are separated spectrally rather than synchronously. In such a system, the choppers shown in c.w. transmitter 134 would not be employed. Rather, separation would be accomplished with high resolution spectral filtering in dual paths, as shown in simultaneous pulse system receiver 116 (FIG. 9). That receiver would be further changed by replacing the dual high speed range gated digitizer with dual analog-to-digital converters.

It should be further understood that the methods described above for generating the desired laser frequencies can be varied in several ways, including providing several stages of amplification to drive the dye lasers (so-called oscillator/amplifier configurations), direct flash lamp pumping rather than laser pumping of a dye laser, or a solid state flash lamp pumped tunable laser, such as Alexandrite in place of the pump/dye configuration. An alternative sequential arrangement could be obtained by switching frequencies with a single dye laser from shot to shot by rotating the dye laser cavity manually or by inserting a wedge element into the cavity, or using electronic switching methods, e.g., Pockel's Cell, Kerr Effect or Bragg Effect (acousto-optic method).

Furthermore, it should also be understood that a single system may be employed utilizing a single reference beam for both a temperature probe beam and a pressure probe beam and where all three are generated by the same system and either alternately or simultaneously.

Moreover, processing of the received signals may include a calibration-based system rather than an algorithm-based system. One such calibration-based system would use predetermined values of absorption coefficient (absorption per unit path) as a function of pressure and temperature, although a given measurement would be primarily sensitive to one or the other. The predetermined values would be stored in a look-up table from which the pressure or temperature could be obtained for any given set of measurements.

In this disclosure, there is shown and described only the preferred embodiments of the invention. It is to be understood, however, that the invention is capable of use in various other modifications and environments and is capable of changes or modifications within the scope of the inventive concept, as expressed herein. For example, it is understood that the invention is not limited to any particular algorithm or equation for obtaining temperature and pressure measurements as a function of beam absorption in the atmosphere, the iterative equation (23) for obtaining temperature disclosed above being merely exemplary. Further, the invention is not limited to any particular mathematical technique for obtaining pressure as a function of absorption, such being derivable, as an ordinary mathematical exercise, from the principles of this invention.

We claim:

1. A remote atmospheric gas temperature measurement method, comprising the steps of:
generating a laser beam at a selected on-line wavelength of 12,999.95 wavenumbers wherein the gas exhibits relatively temperature sensitive and relatively pressure insensitive absorption characteristics;
transmitting said laser beam through a region containing the gas to be measured;
receiving said beam backscattered from at least two ranges;
measuring the energy of said received laser beam from said at least two ranges;
generating a second reference laser beam at a wavelength in the range of 13,000.50–13,001.50 wavenumbers whereat the gas exhibits a substantially non-absorption characteristic;
transmitting said second laser beam colinearly with said first laser beam;
receiving said second laser beam backscattered from said at least two ranges;
measuring the energy of said received second laser beam from said at least two ranges;
determining the fraction of beam energy absorbed by said gas between said at least two ranges using said energy measurements;
processing said determined fraction of beam energy absorbed to obtain a measurement of temperature between said at least two ranges.

2. A remote atmospheric gas pressure measurement method, comprising the steps of:
generating a laser beam at a selected on-line wavelength of 13,153.8 wavenumbers wherein the gas exhibits relatively pressure sensitive and relatively temperature insensitive absorption characteristics;
transmitting said laser beam through a region containing the gas to be measured;
receiving said beam backscattered from at least two ranges;
measuring the energy of said received laser beam from said at least two ranges;
generating a second reference laser beam at a wavelength of 13,152.2 wavenumbers whereat the gas exhibits a substantially non-absorption characteristic;
transmitting said second laser beam colinearly with said first laser beam;
receiving said second laser beam backscattered from said at least two ranges;
measuring the energy of said received second laser beam from said at least two ranges;
determining the fraction of beam energy absorbed by said gas between said at least two ranges using said energy measurements;
processing said determined fraction of beam energy absorbed to obtain a measurement of pressure between said at least two ranges or the pressure at the most remote of said at least two ranges.

3. The method of claim 1 or 2 wherein said processing of said determined fraction of beam energy absorbed includes the use of emperically determined absorption coefficients.

4. The method of claim 1 wherein said temperature sensitive laser beam wavelength corresponds substantially to a region about the center of an absorption line with a relatively high ground state energy of said gas.

5. The method of claim 2 wherein said pressure sensitive wavelength corresponds to a wing of an absorption line having a relatively low ground state energy of said gas.

6. The method of claim 2 wherein said pressure sensitive wavelength is in an absorption trough or minimum absorption region between a pair of absorption lines of said gas.

7. The method of claim 1 or 2 wherein said second laser beam is weakly absorbed relative to the on-line wavelength.

8. The method of claim 1 or 2 where the on-line wavelength and the reference wavelength are sufficiently close in frequency to provide similar backscatter.

9. The method of claim 1 or 2 wherein said gas is oxygen.

10. The method of claim 9 wherein said absorption is in the oxygen "A" band.

11. The method of claim 1 or 2 wherein said transmitted laser beams are normalized for transmitted laser energy.

12. The method of claim 1 or 2 wherein said on-line laser transmission is monitored for laser frequency and line shape.

13. The method of claim 12 wherein said on-line laser frequency monitoring is employed to control the on-line laser frequency.

14. An apparatus for remotely measuring the temperature of a gas, comprising:
means for generating a first laser beam having a wavelength of 12,999.95 wavenumbers whereat said gas exhibits a relatively temperature sensitive and pressure insensitive absorption characteristic;
means for generating a second laser beam having a wavelength in the range of 13,000.5–13,001.5 wavenumbers whereat said gas exhibits a relatively non-temperature and non-pressure sensitive absorption characteristic;
means for transmitting said first and second laser beams colinearly through said gas to be reflected from at least two ranges, said ranges being the same for both the first and second laser beams;
means for receiving said reflected first and second laser beams from said at least two ranges;
means for separating and converting said received first and second beams from said at least two ranges to corresponding first and second electrical signals; and
means for processing said signals to obtain a gas temperature.

15. An apparatus for remotely measuring the pressure of a gas, comprising:
means for generating a first laser beam having a wavelength of 13,153.8 wavenumbers whereat said gas exhibits a relatively pressure sensitive and temperature insensitive absorption characteristic;
means for generating a second laser beam having a wavelength of 13,152.2 wavenumbers whereat said gas exhibits a relatively non-temperature and non-pressure sensitive absorption characteristic;
means for transmitting said first and second laser beams colinearly through said gas to be reflected from at least two ranges, said ranges being the same for both the first and second laser beams;

means for receiving said reflected first and second laser beams from said at least two ranges;

means for separating and converting said received first and second beams from said at least two ranges to corresponding first and second electrical signals; and means for processing said signals to obtain a gas pressure.

16. The apparatus of claim 14 or 15 wherein said first and second laser beams are in the form of pulses.

17. The apparatus of claim 14 or 15 wherein said means for receiving said reflected first and second laser beams includes a range-gated receiver.

18. The apparatus of claim 14 or 15 wherein said first and second laser beams are in the form of continuous wave transmission.

19. The apparatus of claim 14 or 15 wherein said means for receiving said reflected first and second laser beams includes a receiver with a narrow band, synchronous detector.

20. The apparatus of claim 14 or 15 wherein said means for generating the beam energy in said first and second laser beams includes a further means to monitor said energy prior to transmission.

21. The apparatus of claim 14 or 15 wherein said means for generating said first laser beam includes further means to monitor the frequency and line shape of said first laser beam prior to transmission.

22. The apparatus of claim 21 wherein the information from said monitor is employed to control the wavelength of said first laser beam.

23. The apparatus of claim 16 wherein said first and second laser beam pulses are simultaneous.

24. The apparatus of claim 16 wherein said first and second laser beam pulses are generated and transmitted, respectively, sequentially.

25. The apparatus of claims 14 or 15 wherein said means for generating first and second laser beams include:

pump means for generating at least one energizing source;

means connected to said pump means for developing first and second energized transmission paths;

first and second laser means, with inputs and outputs, energizable by said transmission paths at their inputs; and means for combining said laser outputs for colinear transmission.

26. The apparatus of claim 25 wherein said pump means includes at least one solid state laser.

27. The apparatus of claim 25 wherein said first and second laser means are dye lasers.

28. The apparatus of claims 14 or 15 wherein said means for generating first and second laser beams include:

pump means for generating an energizing source;

laser means with an input and a variable frequency output connected to said pump means at said input and;

means for varying the output frequency of said laser means.

29. The apparatus of claims 14 and 15 wherein said first and second laser beams are transmitted in the form of modulated c.w. waves, each of said first and second laser beams being modulated at a different rate and said receiving means further including means for spectral separation of said first and second laser beams.

30. The apparatus of claim 29 wherein said means for spectral separation includes dual synchronous detectors.

31. The apparatus of claim 30 wherein said means for spectral separation includes narrow banding means.

* * * * *